United States Patent [19]
Hollis et al.

[11] Patent Number: 5,880,288
[45] Date of Patent: Mar. 9, 1999

[54] PROCESS FOR THE PREPARATION OF 2-METHYLTHIAZOLE-5-CARBOXYLATES

[75] Inventors: Aggie Hoobler Hollis, Eureka; Gabriel H. Srouji, Kirkwood, both of Mo.

[73] Assignee: Rohm and Haas Company, Phila., Pa.

[21] Appl. No.: 927,981

[22] Filed: Aug. 11, 1992

[51] Int. Cl.⁶ .................................................. C07D 277/04
[52] U.S. Cl. ............................................................ 548/201
[58] Field of Search ............................................. 548/201

[56] References Cited

U.S. PATENT DOCUMENTS

| 3,794,636 | 2/1974 | Girgis | 548/201 |
| 5,045,554 | 9/1991 | Alt et al. | 514/365 |

FOREIGN PATENT DOCUMENTS 0276177   7/1988   European Pat. Off. .

OTHER PUBLICATIONS

Liebscher et al. "Ring Transformation via Bridged 1,3–Dicarbonyl Heteroanalogs Part II." Synthesis, Dec. 1989, pp. 968–970.

*Primary Examiner*—Johann Richter
*Assistant Examiner*—John Dolan
*Attorney, Agent, or Firm*—Thomas D. Rogerson

[57] ABSTRACT

An improved process for the preparation of alkyl 4-halomethyl -2-methylthiazole-5-carboxylate comprising contacting a solution of alkyl 4-(halo)-2-chloroacetoacetate in acetonitrile with thioacetamide in the presence of an amine, such as triethylamine.

12 Claims, No Drawings

PROCESS FOR THE PREPARATION OF 2-METHYLTHIAZOLE-5-CARBOXYLATES

FIELD OF THE INVENTION

The present invention provides an improved process for the production of alkyl 4-halomethyl-2-methlthiazole-5-carboxylates from alkyl 4-(halo)-2-chloroacetoacetate and thioacetamide.

BACKGROUND OF THE INVENTION

It is well known that alkyl 4-(halo)-2-chloroacetoacetate and thioacetamide may be reacted to form alkyl 4-halomethyl-2-methylthiazole-5-carboxylates. The process is actually two reactions—cyclization, followed by dehydration. Previous processes for forming thiazoles involved acid catalyzed dehydration.

U.S. Pat. No. 5,045,554 (Alt et al., 9/91), herein incorporated by reference, discloses the reaction of ethyl 4,4,4-trifluoro-2-chloroacetoacetate and thioacetamide to produce ethyl 2-methyl-4-(trifluoromethyl)thiazole-5-carboxylate, which was in turn used to produce fungicidal thiazolecarboxanilides. The reaction produced the thiazole in one step by refluxing the reactants in dimethylformamide, but had only a 38% isolated yield.

However, a process having higher yields is desired for commercial scale production. It is an object of the present invention to provide such a process. It is a further object of the present invention to provide such a process which also results in shorter cycle times, allowing for greater production capacity. It is a still further object of the present invention to provide such a process which also functions at lower temperatures and thus requires less heating, resulting in energy savings.

DESCRIPTION OF THE INVENTION

The present invention provides a process for the production of alkyl 4-halomethyl-2-methylthiazole-5-carboxylate comprising contacting a solution of alkyl 4-(halo)-2-chloroacetoacetate in acetonitrile with thioacetamide in the presence of an amine, wherein said thioacetamide and amine are each in molar excess to said alkyl 4-(halo)-2-chloroacetoacetate.

The amine may be primary, secondary, or tertiary; an alkyl amine is preferred. Triethylamine is highly preferred.

The molar ratio of thioacetamide is preferably between approximately 1.05 and 2.0 per mole of alkyl 4(halo)-2-chloroacetoacetate, more preferably between approximately 1.1 and 1.5, most preferably about 1.2.

The amine base is also used in molar excess. At least 2.0 equivalents are needed to complete the reaction and more may be used; the minimum amount needed to achieve optimum results is 2.5 equivalents. The base must be added subsequent to the initial contact between thioacetamide and alkyl 4-(halo)-2-chloroacetoacetate in order to obtain the most efficient process.

The thioacetamide used in the present invention may be purchased or separately prepared, or, alternatively, it may be prepared in the same vessel used for the present reaction if it is carried out by the catalyzed reaction of acetonitrile and hydrogen sulfide as disclosed in copending U.S. Ser. No. 07/927,997 C. Williams, filed Aug. 11, 1992, herein incorporated by reference.

As used herein, the term "alkyl" means a straight- or branched-chain alkyl group having from 1 to 6 carbon atoms. As used herein, the term "haloalkyl" means a straight- or branched-chain alkyl group having from 1 to 6 carbon atoms wherein one or more hydrogen atoms have been replaced with an atom selected from chlorine, bromine, iodine, and fluorine. As used herein, the term "halo" means one, two, or three atoms selected from chlorine, bromine, iodine, and fluorine.

The initial temperature is not critical. It may be ambient temperature up to about 60° C. An exotherm may result from the initial mixing of reactants. Heating of the reaction mixture when all ingredients are present is necessary to complete the reaction. The temperature is raised to the reflux temperature of the acetonitrile solution. Approximately one hour at reflux should generally be sufficient to complete the reaction.

EXAMPLES

The present invention results in a reaction which is unexpectedly high yielding. The following examples demonstrate the yields.

Example 1

Preparation of Ethyl 2-ethyl-4-(trifluoromethyl) thiazole-5-carboxylate.

To a 250 mL, 3-necked flask fitted with a mechanical stirrer, thermometer, and a reflux condenser, was charged thioacetamide (9.02 g, 0.12 mol) and 60 mL acetonitrile. To this solution was added ethyl 2-chloro-4,4,4-trifluoroacetoacetate (21.86 g, 0.10 mol) dropwise over a period of 15 minutes. A slight exotherm occurred which raised the temperature to 50° C. The reaction mixture was stirred for two hours at room temperature during which time a yellow solid precipitated. Then triethylamine (35 mL, 0.25 mol) was added dropwise with the evolution of white fumes. The reaction temperature rose to about 50° C. The contents were gently refluxed for one hour during which the color changed from yellow to brown. After cooling, water (25 mL) was added. The mixture was extracted with ether (2 ×100 mL) and washed with 10% HCl (25 mL). After concentration and drying at 1 mm vacuum overnight, the desired compound was isolated as a brown solid, 22.15 g, a 90.6% yield with a 97.8 wt.% purity assay. m.p. 30°–32° C.

Example 2

Preparation of 2-Methyl-4-(trifluoromethyl)thiazole-5-carboxylic acid.

The reaction of Example 1 may be carried out as generally described and the ester may be converted to the acid by conventional methods without isolation. The following is an example of one method.

To a 22 L flask fitted with a mechanical stirrer, thermocouple, and a reflux condenser, was charged thioacetamide (500.6 g, 6.66 mol) and acetonitrile (4 L). This resulted in an endothermic dissolution. To this solution was added ethyl 2-chloro-4,4,4-trifluoroacetoacetate (1105 g, 5.06 mol) over a period of 40 minutes. A slight exotherm occurred which raised the temperature to 55.820 C. The reaction mixture was stirred for 2.3 hours at room temperature during which time a yellow solid precipitated. Then triethylamine (1380 g, 13.64 mol) was added slowly. The reaction temperature rose to about 52° C. The contents were gently refluxed for one hour (internal temperature 75.8° C). After cooling to 46° C., a 40% sodium hydroxide solution (prepared from 1304 g 50% NaOH and 326 mL water, 16.3 mol) was added over 10 minutes. An exotherm to 53.6° C. was noted. The mixture was placed under a vacuum of 95 mm and the solvent distilled from the reaction until only water (of saponification) is present in the distillate. To the remaining reaction mixture was added 2 L water and 1.5 kg ice. Then concentrated HCl (1500 mL, 18 mol) was added over a 15 minute period to bring the pH to less than 2. Another 2 L water and 2 kg ice were added, and the product was filtered, washed on the filter with 12 L water, and dried in a vacuum oven to obtain 2-methyl-4-(trifluoromethyl) thiazole-5-carboxylic acid, 825 g as a beige solid, a 75.4% yield at 97.6% purity.

What is claimed is:

1. A method of producing alkyl 4-halomethyl-2-methylthiazole-5-carboxylate comprising
   a) contacting a solution of alkyl 4-(halo)-2-chloroacetoacetate in acetonitrile with thioacetamide; and
   b) thereafter adding an amine and heating the reaction mixture at reflux until substantially complete;
   wherein said thioacetamide and amine are in molar excess to said alkyl 4-(halo)-2-chloroacetoacetate.

2. The method of claim 1 wherein said amine is triethylamine.

3. The method of claim 2 wherein the ratio of thioacetamide to alkyl 4-(halo)-2-chloroacetoacetate is between approximately 1.05 and 2.0.

4. The method of claim 3 wherein said ratio is approximately 1.2.

5. The method of claim 2 wherein said the ratio of triethylamine to alkyl 4-(halo)-2-chloroacetoacetate is between approximately 2.0 and 3.0.

6. The method of claim 2 wherein said alkyl 4(halo)-2-chloroacetoacetate is ethyl 2-chloro-4,4,4-trifluoroacetoacetate.

7. A method of producing 4-halomethyl-2-methylthiazole-5-carboxylic acid comprising a) contacting a solution of alkyl 4-(halo)-2-chloroacetoacetate in acetonitrile with thioacetamide;
   b) thereafter adding an amine and heating the reaction mixture at reflux until substantially complete; and
   c) thereafter converting the resulting alkyl 4-halomethyl-2-methylthiazole-5-carboxylate to the corresponding 4-halomethyl-2-methylthiazole-5-carboxylic acid;
   wherein said thioacetamide and amine are in molar excess to said alkyl 4-(halo)-2chloroacetoacetate.

8. The method of claim 7 wherein said amine is triethylamine.

9. The method of claim 8 wherein the ratio of thioacetamide to alkyl 4-(halo)-2-chloroacetoacetate is between approximately 1.05 and 2.0.

10. The method of claim 9 wherein said ratio is approximately 1.2.

11. The method of claim 8 wherein said the ratio of triethylamine to alkyl 4-(halo)-2-chloroacetoacetate is between approximately 2.0 and 3.0.

12. The method of claim 8 wherein said alkyl 4-(halo)-2-chloroacetoacetate is ethyl 2-chloro-4,4,4-trifluoroacetoacetate and the resulting 4-halomethyl-2-methylthiazole-5-carboxylic acid is 4-(trifluoromethyl)-2-methylthiazole-5-carboxylic acid.

* * * * *